United States Patent [19]
Filippini et al.

[11] Patent Number: 5,955,319
[45] Date of Patent: Sep. 21, 1999

[54] PROCESS FOR PREPARING DOXORUBICIN

[75] Inventors: Silvia Filippini, Milan; Umberto Breme, Vigevano; Anna Luisa Colombo, Milan, all of Italy; Natasha Lomovskaya, Madison, Wis.; Leonid Fonstein, Madison, Wis.; Sharee Otten, Madison, Wis.; Charles R. Hutchinson, Cross Plains, Wis.

[73] Assignee: Pharmacia & Upjohn, S.p.A., Milan, Italy

[21] Appl. No.: 08/901,306

[22] Filed: Jul. 28, 1997

[51] Int. Cl.⁶ .............................. C12P 19/56; C12N 1/21; C12N 15/63; C12N 15/76
[52] U.S. Cl. ................... 435/78; 435/252.3; 435/252.35; 435/320.1
[58] Field of Search ........................... 435/252.35, 252.3, 435/320.1, 78

[56] References Cited

PUBLICATIONS

Stutzman–Engwall et al., Proc. Natl. Acad. Sci. USA 86:3135–3139 (1989).
Otten et al., J. Bacteriol. 172(6):3427–3434 (1990).
Dickens et al., J. Bacteriol. 178(11):3389–3395 (1996).
Scotti et al., J. Bacteriol. 178(24):7316–7321 (1990).

*Primary Examiner*—Johnny F. Railey, II
*Attorney, Agent, or Firm*—Nikaido Marmelstein Murray & Oram, LLP

[57] ABSTRACT

The present invention concerns a process for improving doxorubicin production by means of a recombinant *Streptomyces peucetius* strain bearing a mutation in the gene dnrU coding for a protein involved in the metabolism of daunorubicin.

10 Claims, 4 Drawing Sheets

SEQ ID 1

ATGACGGCCTCCACCCCGCACGGGACACCCCGCCGGGGGCTGTCCGGCCGCACGGTCCTGGTCACGGGCCATCGCGGGCGCG
CCCTCGGGTCGGGGCCAGGGGCGGGTCGTGCTCGGGCGACTTCGGGGAGGCGACCATCCAGGACGGCTTCGAGGCCACCATCCAG
GGCCCCGACCCCTTCGCGGCACTCCGCCGCCTGCGGGAGCGGCTGGCCGGGTTCCTGGCGCTCCGCCTGATCGCCCGGCTGGCCCGG
AGCAAGGCGGCGGCCATGTTCTGGCGGCGGCCATTGTCGGCCAGGCCATCGAGGTCTGCGCAGTCAATCACTCGGAGCTTCTCTGGCACGGC
TGCTCGGGCAGCGCCTGGCGGGCCTATCCTCACCTGCGCACGGTACACCCAGTCCTGTCAAGGCGACCTCAAGCGGCACCGTCA
CGGCTACACCGGCAGGGTCGGCACCCCGCATCGACGCGCAAACAGGCGCAAGGTGCAGGTCTGGGGTCAGC
TATCACCCGGTGAGGTCGGCAGCGGTGGGGCACGGGTCACTTCGCCTGCTCACCCTCTGCCTGTCAACGGGCTGGGCCTGTCCCGGCAAGGGCCG
ACACCCCGGCCCTCGGAGCTCGGGCCGGGCTGAGCTCTGCTGCCCCCGGCACACCCGGCACTGA

SEQ ID 2

MTASTPHGTPRGLSGRTVLVIGATSGIGRAAALAVARQGARVLVGRDPERLRTVINEVARTAGPAPDAFRADEFAELRQVRDIGERLRDRYPRIDMA
SNAGQMFWSRTTQDGFEATIQVNHLAGFLLARLIRERLAGGRLLITSSDAYTQGRIDPDDLNGDRHRYSAGQAYGTSKQANIMTAEAARFWPSVLAVS
YHPGEVRLTRLGRGTVASSYERENPFLRSAAKGADILWLASAPAELITGGYSDRRLSPVSGPTADAGLAAKLWEAGAAAVGDIAH*

SEQUENCE LISTING

<160> NUMBER OF SEQ ID NOS: 5

<210> SEQ ID NO 1
<211> LENGTH: 864
<212> TYPE: DNA
<213> ORGANISM: Streptomyces peucetius
<220> FEATURE:
<221> NAME/KEY: CDS
<222> LOCATION: (1)..(864)

<400> SEQUENCE: 1

```
atg acg gcc tcc acc ccg cac cac ggg aca cca cgc ggc ggc ctg tcg      48
Met Thr Ala Ser Thr Pro His His Gly Thr Pro Arg Gly Gly Leu Ser
 1               5                   10                  15 ggc cgg acg gtg ctg gtc acc ggg gcc acg tcc ggc atc ggc cgg gcg      96
Gly Arg Thr Val Leu Val Thr Gly Ala Thr Ser Gly Ile Gly Arg Ala
             20                  25                  30 gcg gcc ctc gcg gtc gcc cgc cag ggg gcc cgc gtc gtg ctc gtc ggc     144
Ala Ala Leu Ala Val Ala Arg Gln Gly Ala Arg Val Val Leu Val Gly
         35                  40                  45 cgg gac ccc gag cgt ctg cgg acc gtc acg aac gag gtg gcc cgg acc     192
Arg Asp Pro Glu Arg Leu Arg Thr Val Thr Asn Glu Val Ala Arg Thr
     50                  55                  60 gcc ggc ccg gcc ccg gac gcc ttc cgc gcg gac ttc gcc gag ctg cgc     240
Ala Gly Pro Ala Pro Asp Ala Phe Arg Ala Asp Phe Ala Glu Leu Arg
 65                  70                  75                  80 cag gta cgc gac ctg ggg gag cgg ctg cgg gac cgg tac ccg cgc atc     288
Gln Val Arg Asp Leu Gly Glu Arg Leu Arg Asp Arg Tyr Pro Arg Ile
                 85                  90                  95 gat gtc atg gcc agc aac gcc ggc ggc atg ttc tgg tcg cgc acc acg     336
Asp Val Met Ala Ser Asn Ala Gly Gly Met Phe Trp Ser Arg Thr Thr
            100                 105                 110 acc cag gac ggg ttc gag gcc acc atc cag gtc aat cac ctc gca ggc     384
Thr Gln Asp Gly Phe Glu Ala Thr Ile Gln Val Asn His Leu Ala Gly
        115                 120                 125 ttc ctg ctg gca cgg ctg ctg cgg gag cgg ctc gcg ggc ggg cgg ctg     432
Phe Leu Leu Ala Arg Leu Leu Arg Glu Arg Leu Ala Gly Gly Arg Leu
    130                 135                 140
```

```
atc ctc acc tcg tcc gac gcg tac acc cag ggc cgg atc gac ccg gac      480
Ile Leu Thr Ser Ser Asp Ala Tyr Thr Gln Gly Arg Ile Asp Pro Asp
145             150                 155                 160 gac ctc aac ggc gac cgt cac cgc tac agc gcc ggc cag gcg tac ggc      528
Asp Leu Asn Gly Asp Arg His Arg Tyr Ser Ala Gly Gln Ala Tyr Gly
            165                 170                 175 acg tcc aaa cag gcc aac atc atg acc gcg gcg gag gcc gcc agg cgc      576
Thr Ser Lys Gln Ala Asn Ile Met Thr Ala Ala Glu Ala Ala Arg Arg
        180                 185                 190 tgg ccg gac gtg ctg gcg gtc agc tat cac ccc ggt gag gtc cgc acc      624
Trp Pro Asp Val Leu Ala Val Ser Tyr His Pro Gly Glu Val Arg Thr
    195                 200                 205 cgc atc gga cgg ggc acg gtc gcc tcg tcc tac ttc cgg ttc aac ccc      672
Arg Ile Gly Arg Gly Thr Val Ala Ser Ser Tyr Phe Arg Phe Asn Pro
210                 215                 220 ttc ctg cgc tcc gcg gcg aag ggc gcc gac acc ctc gtg tgg ctg gcg      720
Phe Leu Arg Ser Ala Ala Lys Gly Ala Asp Thr Leu Val Trp Leu Ala
225                 230                 235                 240 tcc gcg ccg gcc gag gag ttg acc acg ggc ggc tac tac agc gac cgg      768
Ser Ala Pro Ala Glu Glu Leu Thr Thr Gly Gly Tyr Tyr Ser Asp Arg
                245                 250                 255 cgg ctg tcc ccg gtg agc ggc ccg acc gcc gac gcc ggc ctc gcg gcg      816
Arg Leu Ser Pro Val Ser Gly Pro Thr Ala Asp Ala Gly Leu Ala Ala
            260                 265                 270 aag ctc tgg gag gcc ggc gcg gcc gcc gtc ggc gac acc gcg cac tga      864
Lys Leu Trp Glu Ala Gly Ala Ala Ala Val Gly Asp Thr Ala His
        275                 280                 285

<210> SEQ ID NO 2
<211> LENGTH: 287
<212> TYPE: PRT
<213> ORGANISM: Streptomyces peucetius

<400> SEQUENCE: 2

Met Thr Ala Ser Thr Pro His His Gly Thr Pro Arg Gly Gly Leu Ser
1               5                   10                  15

Gly Arg Thr Val Leu Val Thr Gly Ala Thr Ser Gly Ile Gly Arg Ala
            20                  25                  30
Ala Ala Leu Ala Val Ala Arg Gln Gly Ala Arg Val Val Leu Val Gly
        35                  40                  45

Arg Asp Pro Glu Arg Leu Arg Thr Val Thr Asn Glu Val Ala Arg Thr
    50                  55                  60
Ala Gly Pro Ala Pro Asp Ala Phe Arg Ala Asp Phe Ala Glu Leu Arg
65                  70                  75                  80

Gln Val Arg Asp Leu Gly Glu Arg Leu Arg Asp Arg Tyr Pro Arg Ile
                85                  90                  95
Asp Val Met Ala Ser Asn Ala Gly Met Phe Trp Ser Arg Thr Thr
                100                 105                 110

Thr Gln Asp Gly Phe Glu Ala Thr Ile Gln Val Asn His Leu Ala Gly
            115                 120                 125
Phe Leu Leu Ala Arg Leu Leu Arg Glu Arg Leu Ala Gly Gly Arg Leu
        130                 135                 140

Ile Leu Thr Ser Ser Asp Ala Tyr Thr Gln Gly Arg Ile Asp Pro Asp
145                 150                 155                 160
Asp Leu Asn Gly Asp Arg His Arg Tyr Ser Ala Gly Gln Ala Tyr Gly
                165                 170                 175

Thr Ser Lys Gln Ala Asn Ile Met Thr Ala Ala Glu Ala Ala Arg Arg
            180                 185                 190
Trp Pro Asp Val Leu Ala Val Ser Tyr His Pro Gly Glu Val Arg Thr
        195                 200                 205
```

```
Arg Ile Gly Arg Gly Thr Val Ala Ser Ser Tyr Phe Arg Phe Asn Pro
        210                 215                 220
Phe Leu Arg Ser Ala Ala Lys Gly Ala Asp Thr Leu Val Trp Leu Ala
225                 230                 235                 240
Ser Ala Pro Ala Glu Glu Leu Thr Thr Gly Gly Tyr Tyr Ser Asp Arg
                245                 250                 255
Arg Leu Ser Pro Val Ser Gly Pro Thr Ala Asp Ala Gly Leu Ala Ala
            260                 265                 270
Lys Leu Trp Glu Ala Gly Ala Ala Val Gly Asp Thr Ala His
        275                 280                 285

<210> SEQ ID NO 3
<211> LENGTH: 1569
<212> TYPE: DNA
<213> ORGANISM: Streptomyces peucetius
<220> FEATURE:
<221> NAME/KEY: CDS
<222> LOCATION: (1)..(255)
<220> FEATURE:
<221> NAME/KEY: CDS
<222> LOCATION: (1219)..(1569)

<400> SEQUENCE: 3
```

| | | |
|---|---|---|
| atg gct gag ctc agc ctg gcg gaa ctg cgg gag atc atg cgg cag agc<br>Met Ala Glu Leu Ser Leu Ala Glu Leu Arg Glu Ile Met Arg Gln Ser<br>1               5                   10                  15 | | 48 |
| ctg ggg gag gac gag gtc ccc gac ctt gcg gac gcg gac acc gtg acc<br>Leu Gly Glu Asp Glu Val Pro Asp Leu Ala Asp Ala Asp Thr Val Thr<br>            20                  25                  30 | | 96 |
| ttc gag gac ctc ggg ctc gac tcc ctg gcc gtc ctg gaa acg gtc aac<br>Phe Glu Asp Leu Gly Leu Asp Ser Leu Ala Val Leu Glu Thr Val Asn<br>        35                  40                  45 | | 144 |
| cac atc gag cgg acc tat ggc gtg aag ctg ccc gag gag gaa ctg gcg<br>His Ile Glu Arg Thr Tyr Gly Val Lys Leu Pro Glu Glu Glu Leu Ala<br>    50                  55                  60 | | 192 |
| gag gtc agg acg ccg cat agc atg ctg atc ttc gtc aac gag agg ctg<br>Glu Val Arg Thr Pro His Ser Met Leu Ile Phe Val Asn Glu Arg Leu<br>65                  70                  75                  80 | | 240 |
| cga gcg gcg gca tga cggcctccac cccgcaccac gggacaccac gcggcggcct<br>Arg Ala Ala Ala | | 295 |
| gtcgggccgg acggtgctgg tcaccggggc cacgtccggc atcggccggg cggcggccct | | 355 |
| cgcggtcgcc cgccaggggg cccgcgtcgt gctcgtcggc cgggaccccg agcgtctgcg | | 415 |
| gaccgtcacg aacgaggtgg cccggaccgc cggcccggcc ccgacgcct tccgcgcgga | | 475 |
| cttcgccgag ctgcgccagg tacgcgacct ggggagcgg ctgcgggacc ggtacccgcg | | 535 |
| catcgatgtc atggccagca acgccggcg catgttctgg tcgcgcacca cgacccagga | | 595 |
| cgggttcgag gccaccatcc aggtcaatca cctcgcaggc ttcctgctgg cacggctgct | | 655 |
| gcgggagcgg ctcgcgggcg gcggctgat cctcacctcg tccgacgcgt acacccaggg | | 715 |
| ccggatcgac ccggacgacc tcaacggcga ccgtcaccgc tacagcgccg gccaggcgta | | 775 |
| cggcacgtcc aaacaggcca acatcatgac cgcggcggag ccgccaggc gctggccgga | | 835 |
| cgtgctggcg gtcagctatc accccggtga ggtccgcacc cgcatcggac ggggcacggt | | 895 |
| cgcctcgtcc tacttccggt tcaaccccttc cctgcgctcc gcggcgaagg gcgccgacac | | 955 |
| cctcgtgtgg ctggcgtccg cgccggccga ggagttgacc acgggcggct actacagcga | | 1015 |
| ccggcggctg tccccggtga gcggcccgac cgccgacgcc ggcctcgcgg cgaagctctg | | 1075 |
| ggaggccggc gcgccgccg tcggcgacac cgcgcactga cggcggcggc ccgccccgcc | | 1135 |
| cgcatgtccg tctcatccgc gagatgtccg tctcatccgc gagcgcagac gctcgtgtgc | | 1195 |

```
cgatccatcg aaaggaacga ttc gtg acc agg ttc gcg ccc ggc gcc ccc gca      1248
                         Val Thr Arg Phe Ala Pro Gly Ala Pro Ala
                          85                  90 tgg ttc gac ctc ggt tcg ccc gat gtc gcc gcc tcg gcc gac ttc tac      1296
Trp Phe Asp Leu Gly Ser Pro Asp Val Ala Ala Ser Ala Asp Phe Tyr
 95                 100                 105                 110 acc ggc ctg ttc ggc tgg acc gcc acc gtg gtc agc gac ccg ggc gcc      1344
Thr Gly Leu Phe Gly Trp Thr Ala Thr Val Val Ser Asp Pro Gly Ala
                115                 120                 125 ggg gga tac acg acg ttc agc tcc gac ggg aag ctg gtc gcc gcg gtc      1392
Gly Gly Tyr Thr Thr Phe Ser Ser Asp Gly Lys Leu Val Ala Ala Val
            130                 135                 140 gcc cgc cac cag atc gac acc ccc tac cac cgg ccg tac ggg ccc ggg      1440
Ala Arg His Gln Ile Asp Thr Pro Tyr His Arg Pro Tyr Gly Pro Gly
        145                 150                 155 aac gac cag cac ggc atg ccg gcc atc tgg acc gtg tac ttc gcc acc      1488
Asn Asp Gln His Gly Met Pro Ala Ile Trp Thr Val Tyr Phe Ala Thr
160                 165                 170 gac gac gcc gac gca ctg acc aag cgg gtc gag acg gcg ggc ggc gag      1536
Asp Asp Ala Asp Ala Leu Thr Lys Arg Val Glu Thr Ala Gly Gly Glu
175                 180                 185                 190 gtc atc atg act ccg atg gac gtc ctc ggc ctc                          1569
Val Ile Met Thr Pro Met Asp Val Leu Gly Leu
                195                 200
```

<210> SEQ ID NO 4
<211> LENGTH: 84
<212> TYPE: PRT
<213> ORGANISM: Streptomyces peucetius

<400> SEQUENCE: 4

```
Met Ala Glu Leu Ser Leu Ala Glu Leu Arg Glu Ile Met Arg Gln Ser
 1               5                  10                  15

Leu Gly Glu Asp Glu Val Pro Asp Leu Ala Asp Ala Asp Thr Val Thr
            20                  25                  30

Phe Glu Asp Leu Gly Leu Asp Ser Leu Ala Val Leu Glu Thr Val Asn
        35                  40                  45

His Ile Glu Arg Thr Tyr Gly Val Lys Leu Pro Glu Glu Glu Leu Ala
    50                  55                  60

Glu Val Arg Thr Pro His Ser Met Leu Ile Phe Val Asn Glu Arg Leu
65                  70                  75                  80

Arg Ala Ala Ala
```

<210> SEQ ID NO 5
<211> LENGTH: 117
<212> TYPE: PRT
<213> ORGANISM: Streptomyces peucetius

<400> SEQUENCE: 5

```
Val Thr Arg Phe Ala Pro Gly Ala Pro Ala Trp Phe Asp Leu Gly Ser
 1               5                  10                  15

Pro Asp Val Ala Ala Ser Ala Asp Phe Tyr Thr Gly Leu Phe Gly Trp
            20                  25                  30

Thr Ala Thr Val Val Ser Asp Pro Gly Ala Gly Gly Tyr Thr Thr Phe
        35                  40                  45

Ser Ser Asp Gly Lys Leu Val Ala Ala Val Ala Arg His Gln Ile Asp
    50                  55                  60

Thr Pro Tyr His Arg Pro Tyr Gly Pro Gly Asn Asp Gln His Gly Met
65                  70                  75                  80
```

-continued

```
Pro Ala Ile Trp Thr Val Tyr Phe Ala Thr Asp Asp Ala Asp Ala Leu
            85                  90                  95

Thr Lys Arg Val Glu Thr Ala Gly Gly Glu Val Ile Met Thr Pro Met
            100                 105                 110

Asp Val Leu Gly Leu
        115
```

PROCESS FOR PREPARING DOXORUBICIN

FIELD OF THE INVENTION

The present invention concerns a process for improving doxorubicin production by means of a recombinant strain bearing a mutation in a gene of daunorubicin metabolism.

BACKGROUND OF THE INVENTION

Anthracyclines of daunorubicin group such as doxorubicin, carminomycin and aclacinomycin and their synthetic analogs are among the most widely employed agents in antitumoral therapy (F. Arcamone, Doxorubicin, Academic Press New York, 1981, pp. 12–25; A. Grein, Process Biochem., 16: 34, 1981; T. Kaneko, Chimicaoggi May 11, 1988; C. E. Myers et al., "Biochemical mechanism of tumor cell kill" in Anthracycline and Anthracenedione-Based Anti-cancer Agents (Lown, J. W., ed.) Elsevier Amsterdam, pp. 527–569, 1988; J. W. Lown, Pharmac. Ther. 60: 185–214, 1993). Anthracyclines of the daunorubicin group are naturally occurring compounds produced by various Streptomyces species and by *Actinomyces carminata*. Doxorubicin is mainly produced by strains of *Streptomyces peucetius* while daunorubicin is produced by many other Actinomycetes. In particular daunorubicin and doxorubicin are synthesized in *S. peucetius* ATCC 29050 and 27952 from malonic acid, propionic acid and glucose by the pathway summarized in Grein (Advan. Applied Microbiol. 32: 203, 1987) and in Eckart and Wagner (J. Basic Microbiol. 28: 137, 1988). Aklavinone (11-deoxy-e-rhodomycinone), e-rhodomycinone and carminomycin are established intermediates in this process. The final step in this pathway involves the hydroxylation of daunorubicin to doxorubicin by the DoxA enzyme ({U.S. Ser. No. 08/396,218, WO96/27014}; M. L. Dickens and W. R. Strohl, J. Bacteriol. 178: 3389 (1996)), which is reported to occur only in *S. peucetius*.

Figure 1:
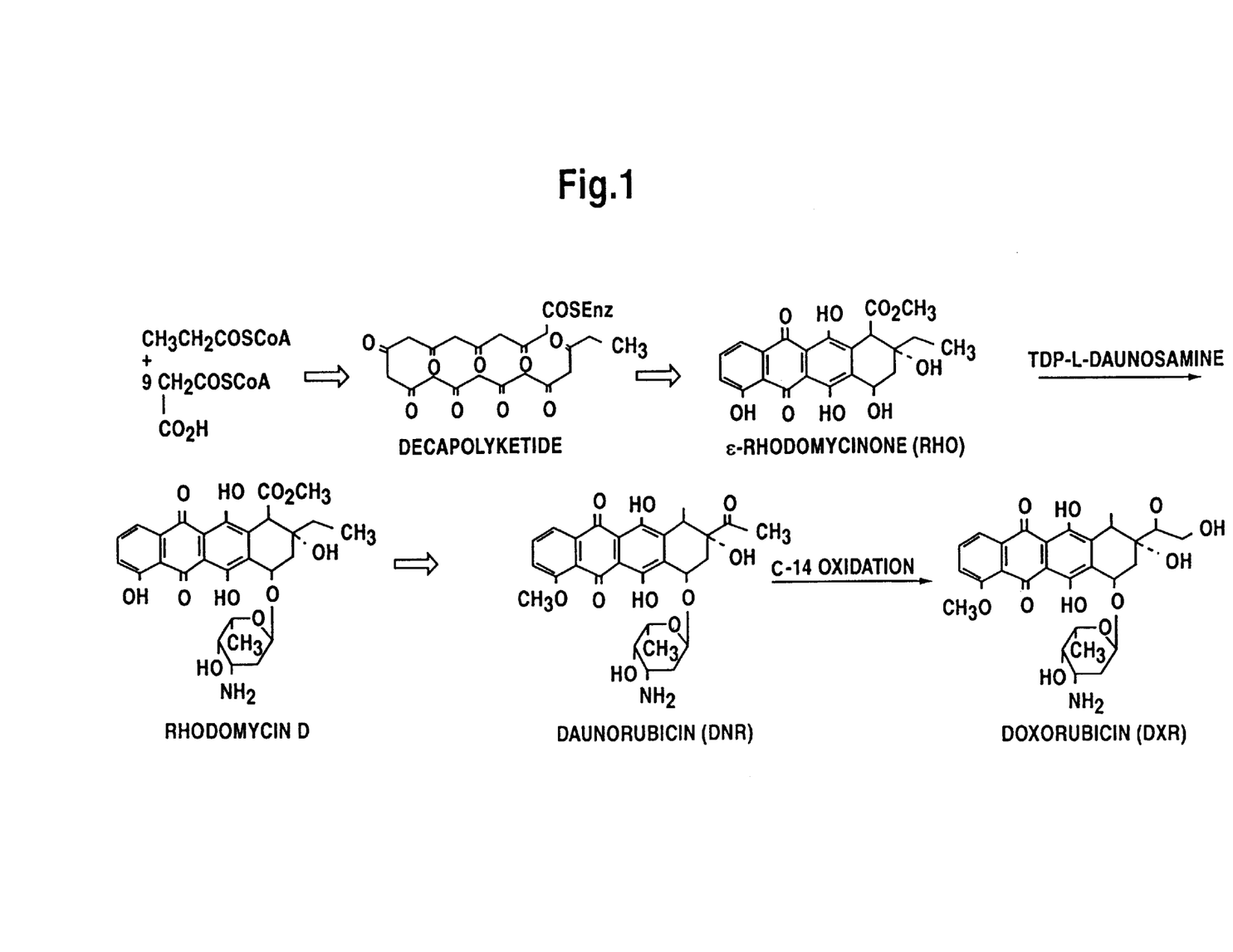
FIG. 1 is a summary of the biosynthetic pathway to daunorubicin and doxorubicin in *S. peucetius*.

13-Dihydrodaunorubicin may be an intermediate in the conversion of e-rhodomycinone to daunorubicin via rhodomycin D (FIG. 1) according to Dickens et al. (J. Bacteriol. 179: 2641 (1997)). Daunorubicin is bioconverted to (13S)-13-dihydrodaunorubicin when added to cultures of *S. peucetius* and some other streptomycetes (N. Crespi-Perellino et al., Experientia, 38: 1455, 1982; T. Oki et al., J. Antibiotics, 34: 1229, 1981; G. Cassinelli et al., Gazz. Chim. Ital. 114: 185, 1984). It is not known whether the 13-dihydrodaunorubicin that may be an intermediate of daunorubicin and doxorubicin production in *S. peucetius* is identical to the (13S)-13-dihydrodaunorubicin formed by this bioconversion. Since these two compounds can differ in their C-13 stereochemistry, one diastereomer of 13-dihydrodaunorubicin might be a substrate for DoxA and the other one would not. In the latter case, C-13 reduction of daunorubicin would block its further oxidation to doxorubicin.

Several genes for daunorubicin and doxorubicin biosynthesis and resistance have been isolated from *S. peucetius* 29050 and 27952 by cloning experiments. The *S. peucetius* dnrU gene identified herein is a homolog of the Streptomyces sp. strain C5 gene ORF1 (syn. dauU) described by Dickens and Strohl (J. Bacteriol. 178: 3389 (1996)). Since the predicted protein products of the dnrU and dauU genes resemble enzymes known to reduce ketone groups, the DnrU and DauU proteins may catalyze the reduction of daunorubicin, formed in vivo or added to cultures exogenously, to 13-dihydrodaunorubicin.

SUMMARY OF THE INVENTION

The present invention concerns a process for preparing doxorubicin by means of a bacterial recombinant strain bearing a mutation blocking the function of a gene of daunorubicin metabolism. With this process the amount of doxorubicin is greatly increased, relative to the amount of daunorubicin formed. The relative amounts of e-rhodomycinone, daunorubicin and 13-dihydrodaunorubicin may also be altered, as an incidental consequence of the mutation. Preferably the bacteria is a strain of Streptomyces sp. producing daunorubicin and doxorubicin, having a mutation blocking the function of a gene of daunorubicin metabolism. Said blocked gene is preferably comprised in the DNA fragment having the configuration of restriction sites shown in FIG. 3 or in a fragment derived therefrom containing a gene, dnrU [SEQ ID NO:1], coding for a protein involved in the metabolism of daunorubicin. The present invention provides a mutant strain of *S. peucetius*, obtained from *S. peucetius* ATCC 29050, having a mutation blocking the function of the dnrU gene. This mutation greatly increases the doxorubicin production level relative to the amount of daunorubicin, and by coincidence may also increase the amount of e-rhodomycinone and reduce the amount of 13-dihydrodaunorubicin formed.

Genes for daunorubicin and doxorubicin biosynthesis and resistance have been obtained from *S. peucetius* 29050 and *S. peucetius* 27952 by cloning experiments as described in Stutzman-Engwall and Hutchinson (Proc. Natl. Acad. Sci. USA, 86: 3135 (1988)) and Otten et al., (J. Bacteriol. 172: 3427 (1990)).

The dnrU mutant can be obtained by disrupting the dnrU gene, obtained from the *S. peucetius* 29050 anthracycline production genes described by Stutzman-Engwall and Hutchinson (Proc. Natl. Acad. Sci. USA, 86: 3135 (1988)) and Otten et al. (J. Bacteriol. 172: 3427 (1990)), by insertion of the neomycin/kanamycin resistance gene (aphII) into the BalI restriction site located at the beginning of dnrU. This disrupted dnrU::aphII gene is used to replace the normal dnrU gene in the 29050 strain.

BRIEF DESCRIPTION OF THE DRAWINGS

FIG. 3 is a restriction map analysis of the DNA of the invention. Said DNA is a 4.8-kb BamHI-NruI fragment containing dnrU and dnrV, subcloned from the cosmid clone pWHM335 described in Stutzman-Engwall and Hutchinson, (Proc. Natl. Acad. Sci. USA, 86: 3135 (1988)) and Otten et al. (J. Bacteriol. 172: 3427 (1990)). The location and direction of transcription of the two genes are indicated by arrows. The fragment was inserted into the unique BamHI and NruI restriction sites of the polylinker region of plasmid pSE380 (Invitrogen Corp.). The map shown in FIG. 3 does not necessarily provide an exhaustive listing of all restriction sites present in the DNA fragment. However, the reported sites are sufficient for an unambiguous recognition of the DNA segment. (Restriction site abbreviations: Ba, BamHI;

Sa, SalI, Kp, KpnI; No, NotI; B, BalI, Nr, NruI; Aa, AatII, Ss, SStI and Pv, PvuII).

FIG. 4 is the structure of KC515 and phWHM295 containing the disrupted copy the dnrU gene. ΔattP and cos indicate the relative locations of the deletion in the phage attachment site and the cohesive end of KC515, respectively; tsr, vph and aphII are the thiostrepton, viomycin and neomycin resistance genes, respectively. (Restriction site abbreviations: Ba, BamHI; Bg, BglII; Hp, HpaII; No, NotI; Nr, NruI; Ps PstI; Pv, PvuII; SS, SstI and Xh, XhoI).

DESCRIPTION OF THE INVENTION

The present invention provides a bacterial recombinant strain bearing a mutation inactivating the function of the daunorubicin metabolism gene dnrU. The bacterial strain may be one that is daunorubicin- or doxorubicin-sensitive, i.e. cannot grow in the presence of a certain amount of daunorubicin or doxorubicin, or that is daunorubicin- or doxorubicin-resistant. Strains belonging to the Streptomyces genus constitute a preferred embodiment of the invention; a Streptomyces peucetius strain constitutes a particularly preferred embodiment of the invention. Most preferred is the S. peucetius strain WMH1658. The strain WMH1658 was deposited on Jul. 3, 1997 at the American Type Culture Collection, 10801 University Boulevard, Manassas, Va. 20110-2209, USA, under the accession number ATCC 55994. The WMH1658 strain has been obtained from S. peucetius ATCC 29050 strain by replacing the dnrU gene with a mutated dnrU gene into which the neomycin/ kanamycin resistance gene (aphII) from the pFDNEO-S plasmid described by F. Danis and R. Brzezinski, (FEMS Microbiology Letters 81: 261 (1991) has been inserted. The aphII gene has been inserted into the BalI restriction site located at the beginning of dnrU to disrupt the function of dnrU, as better explained in Example 1.

The expert in the art will recognize that any other technique to inactivate the gene can be suitably employed in the present invention.

The bacterial recombinant strain may be any other microorganism transformed with plasmids or transfected with phage DNA containing an anthracycline gene cluster able to produce daunorubicin and/or doxorubicin and/or baumycins.

In another aspect, the present invention provides a process for preparing doxorubicin, which process comprises:

(i) culturing a bacterial recombinant strain of the invention, and (ii) isolating doxorubicin from the culture.

In this process the bacterial recombinant strain may be cultured at from 20 to 40° C., for example from 26 to 37° C. The culture is preferably carried out with agitation. In order to obtain the bacterial recombinant strain of the invention, the dnrU gene was isolated from clones described in Stutzman-Engwall and Hutchinson, (Proc. Acad. Sci. USA 86: 3135 (1989) and Otten et al., (J. Bacteriol. 172: 3427 (1990).

The dnrU gene is contained in a 4.8-kb BamHI-NruI fragment obtained from the cosmid clone pWHM335 described in Stutzman-Engwall and Hutchinson (Proc. Natl. Acad. Sci. USA, 86: 3135 (1988)) and Otten et al. (J. Bacteriol. 172: 3427 (1990)).

Figure 2A:
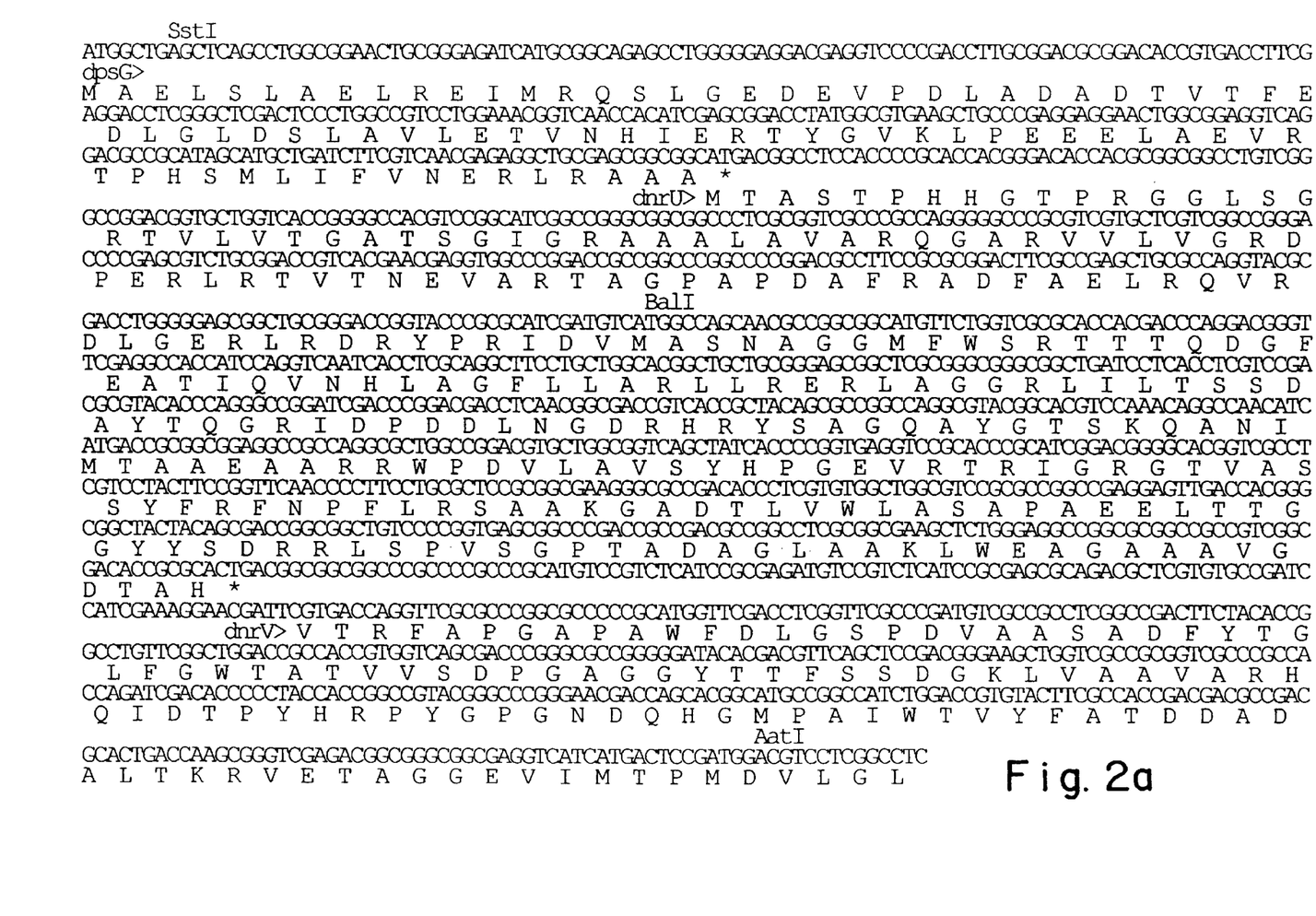
FIG. 2 shows the DNA and deduced protein sequences of the dnrU gene and part of the dnrV gene. SEQ ID 1 is a schematic illustration of the dnrU DNA nucleotide sequence. Said DNA corresponds to that encoding a protein for daunorubicin metabolism. The sequence covers the region between the SstI and the AatII restriction sites and shows the coding strand in the 5' and 3' direction. The derived amino acid sequence of the translated open reading frame encoding a protein required for daunorubicin metabolism is shown below the nucleotide sequence of the dnrU gene as SEQ ID 2.
Figure 2B:
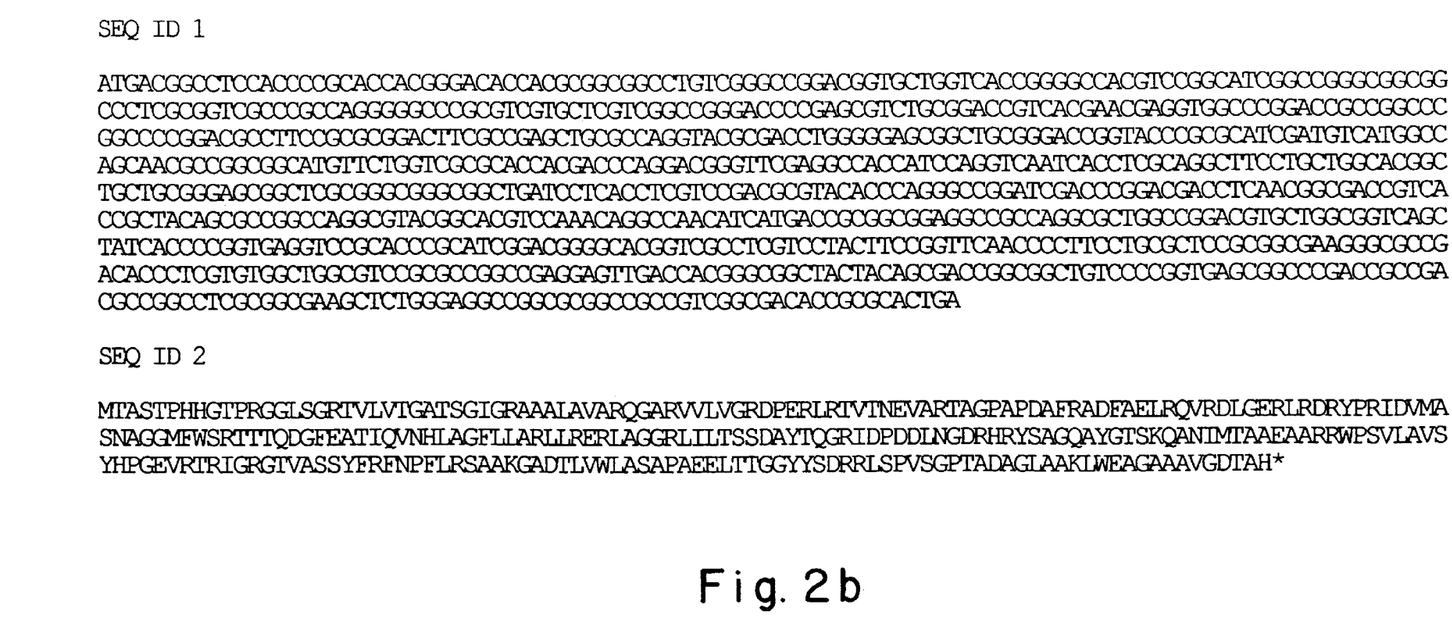

This 4.8 kb BamHI-NruI fragment can be further digested to give the 1.55 kb SstI-AatI fragment whose sequence is shown in FIG. 2. The 1.55 kb SstI-AatI fragment includes the dnrU gene and part of the dnrV gene.

The dnrU gene consists essentially of the sequence of SEQ ID NO 1, which sequence will be referred to as the "dnrU" sequence. The deduced amino acid sequence of the daunorubicin and doxorubicin metabolism protein encoded by SEQ ID NO 1 is shown in SEQ ID NO 2. The isolated dnrU gene was subsequently subcloned into an appropriate DNA cloning vector. Any autonomously replicating and/or integrating agent comprising a DNA molecule to which one or more additional DNA segments can be added may be used. Typically, however, the vector is a plasmid. Preferred plasmids are pUC19 (Yanish-Perron et al., Gene 33: 103 (1985)) and pWHM3 (Vara et al., J. Bacteriol. 171: 5872 (1989)). Any suitable technique may be used to insert the DNA into the vector. Insertion can be achieved by ligating the DNA into a linearized vector at an appropriate restriction site. For this, direct combination of sticky or blunt ends, homopolymer tailing, or the use of a linker or adapter molecule may be employed. The recombinant plasmid is then digested with a suitable restriction enzyme and ligated with the aphII gene. This construction is transferred into a suitable vector for homologous integration. Among the possible vectors that can be used, KC515 (Hopwood et al., Genetic Manipulation of Streptomyces. A Laboratory Manual, John Innes Foundation, Norwich, UK, 1985)) or pKC1139 (M. Bierman et al., Gene 116: 43–49 (1992)) are preferred. KC515 is a derivative of φC31 and can only transduce a host to antibiotic resistance if the vector carries a segment of homologous DNA, and pKC 1139 is an E. coli-Streptomyces shuttle vector that contains a temperature-sensitive replicon that functions well at temperature below 34° C. and bears the apramycin resistance gene. The recombinant vector thus obtained is used to transform, typically with KC515 by transduction with infective phage particles or with pKC119 by protoplast transformation, an appropriate Streptomyces strain; the final step in this inactivation protocol is the isolation of kanamycin resistant transformant in which the recombinant plasmid has recombined with the dnrU gene and inactivated it (see also Example 1).

On the basis of the information provided herein, the expert in the art can easily obtain the 1.55 kb SstI-AatII DNA fragment by:

a) preparing a library of the genomic DNA of S. peucetius 29050 or a strain derived therefrom:

b) screening the library for clones positive to a labelled probe, of at least 24 nucleotides, synthesized according to the sequence of SEQ ID NO: 1;

c) obtaining an insert DNA, from a recombinant vector, that forms part of the library and that has been screened as positive for the ability to metabolize daunorubicin to doxorubicin in the S. peucetius dnrU mutant.

To obtain the DNA fragment, the library may be prepared in step a) by partially digesting the genomic DNA of S. peucetius 29050 or a strain derived therefrom; or by screening a library of Streptomyces genomic DNA that has been enriched for the cluster of daunorubicin and doxorubicin biosynthesis genes. Generally the restriction enzyme MboI is preferably used for genomic DNA, but for the libraries containing the cluster of daunorubicin biosynthesis genes, the restriction enzymes BamHI is preferred. The DNA fragments thus obtained can be size fractionated; fragments from 1 to 7 kb in size are preferred for libraries containing the cluster of daunorubicin and doxorubicin biosynthesis genes. These fragments are ligated into a linearized vector such as pWHM3 or pKC505 ((M. A. Richardson et al, Gene 61: 231 (1987)). E. coli DH5a and DH1 are respectively transformed or transfected with the ligation mixtures.

In step b) the colonies obtained by the transformations are transferred to nylon membranes and screened by colony hybridization for plasmids or cosmids which hybridized to the labelled probe, of at least 24 nucleotides, synthesized according to the sequence of SEQ ID No:1

In step c) plasmid DNA from the clones which hybridized to the probe is isolated and used to transform protoplasts of host cells. The hosts may be microorganisms that produce less doxorubicin than daunorubicin. The S. peucetius dnrU mutant strain (ATCC 55994) that produces more doxorubicin than daunorubicin and, coincidentally, more e-rhodomycinone than the 29050 strain, represents a particularly suitable host.

Clones containing DNA fragments which include the 1.55 kb SstI-AatII DNA fragment of the invention, when introduced into the S. peucetius dnrU mutant strain (ATCC 55994), are recognized by the appearance in fermentation cultures of decreased levels of doxorubicin relative to daunorubicin and, coincidentally, e-rhodomycinone.

MATERIALS AND METHODS

Bacterial strains and plasmids: E. coli strain DH5a (Sambrook et al., Molecular cloning. A laboratory Manual, 2nd ed. Cold Spring Harbor Press, Cold Spring Harbor, N.Y., 1989), which is sensitive to ampicillin, is used for subcloning DNA fragments. S. peucetius ATCC 29050 and a S. peucetius dnrU mutant that produces more doxorubicin than daunorubicin and, coincidentally, more e-rhodomycinone than the 29050 strain are used for disruption and expression, respectively, of the dnrU gene. Streptomyces lividans TK24 (D. A. Hopwood et al., J. Gen. Microbiol. 129: 2257 (1983)) and S. lividans TK24(φC31) lysogen are used in transferction experiments (Hopwood et al., Genetic Manipulation of Streptomyces. A Laboratory Manual, John Innes Foundation, Norwich, UK, 1985) and for screening of phage carrying a cloned chromosomal DNA fragment (N. D. Lomovskaya et al., J. Bacteriol. 178: 3238 (1996) or N. D. Lomovskaya et al. Microbiology 143: 875 (1997)).

The plasmid cloning vectors are pUC18/19 ((Yanish-Perron et al., Gene 33: 103 (1985)), pSE380 (Invitrogen Corp.), pSP72 (Promega), and pWHM3 (Vara et al., J. Bacteriol. 171: 5872 (1989)). The integrative vector is KC515, a derivative of phage φC31 (Hopwood et al., Genetic Manipulation of Streptomyces. A Laboratory Manual, John Innes Foundation, Norwich, UK, 1985). The pFDNEO-S plasmid described by F. Danis and R. Brzezinski, (FEMS Microbiology Letters 81: 261–264 (1991)) is used to get the neomycin/kanamycin aphII resistance gene.

Media and buffer: E. coli strain DH5a is maintained on LB agar (Sambrook et al., Molecular cloning. A laboratory Manual, 2nd ed. Cold Spring Harbor Press, Cold Spring Harbor, N.Y., 1989). When selecting for transformants, ampicillin is added at a concentration of 100 micrograms/ml. S. peucetius 29050 and dnrU::aphII strains are maintained on ISP4 agar (Difco Laboratories, Detroit, Mich.) for the preparation of spores and on R2YE agar (Hopwood et al., Genetic Manipulation of Streptomyces. A Laboratory Manual, John Innes Foundation, Norwich, UK, 1985) for regeneration of protoplasts. When selecting for transformants overlay with 20 micrograms/ml thiostrepton is used. R2YE agar without sucrose is used when S. peucetius 29050 is infected with phage phWHM295.

Subcloning DNA fragments: DNA samples are digested with appropriate restriction enzymes and separated on agarose gel by standard methods (Sambrook et al., Molecular cloning. A Laboratory Manual, 2nd ed. Cold Spring Harbor Press, Cold Spring Harbor, N.Y., 1989). Agarose slices containing DNA fragments of interest are excised from a gel and the DNA is isolated from these slices using the GENECLEAN device (Bio101, La Jolla, Calif.) or an equivalent. The isolated DNA fragments are subcloned using standard techniques (Sambrook et al., Molecular cloning. A Laboratory Manual, 2nd ed. Cold Spring Harbor Press, Cold Spring Harbor, N.Y., 1989) into E. coli for routine manipulations, including DNA sequencing, and E. coli-Streptomyces shuttle vectors for expression experiments and fermentations.

Transformation of E. coli and Streptomyces species: Competent cells of E. coli are prepared by the calcium chloride method (Sambrook et al., Molecular cloning. A Laboratory Manual, 2nd ed. Cold Spring Harbor Press, Cold Spring Harbor, N.Y., 1989) and transformed by standard techniques (Sambrook et al., Molecular cloning. A Laboratory Manual, 2nd ed. Cold Spring Harbor Press, Cold Spring Harbor, N.Y., 1989). S. peucetius dnrU::aphII mycelium is grown in R2YE medium (Hopwood et al., Genetic Manipulation of Streptomyces. A Laboratory Manual, John Innes Foundation, Norwich, UK, 1985) and harvested after 24 hr. The mycelial pellet is washed twice with 10.3% (wt/vol) sucrose solution and used to prepare protoplasts according to the method outlined in the Hopwood manual (Hopwood et al., Genetic Manipulation of Streptomyces. A Laboratory Manual, John Innes Foundation, Norwich, UK, 1985). The protoplast pellet is suspended in about 300 microlitres of P buffer (Hopwood et al., Genetic Manipulation of Streptomyces. A Laboratory Manual, John Innes Foundation, Norwich, UK, 1985) and 50 microlitres aliquot of this suspension is used for each transformation. Protoplasts are transformed with plasmid DNA according to the small scale transformation method of Hopwood et al. (Genetic Manipulation of Streptomyces. A Laboratory Manual, John Innes Foundation, Norwich, UK, 1985), Stutzman-Engwall and Hutchinson (Proc. Natl. Acad. Sci. USA, 86: 3135 (1988) or Otten et al. (J. Bacteriol. 172: 3427 (1990)). After 17 hr of regeneration on R2YE medium at 30° C., the plates are overlayed with 20 micrograms/ml of thiostrepton and allowed to grow at 30° C. until sporulated.

Doxorubicin and daunorubicin production: S. peucetius dnrU::aphII is inoculated into 25 ml of liquid R2YE medium with 40 micrograms/ml of kanamycin sulfate in a 300 ml flask and incubated at 30° C. and 300 rpm on a rotary shaker. After 2 days of growth 2.5 ml of this culture are transferred to 25 ml of APM production medium: ((g/l) glucose (60), yeast extract (8), malt extract (20), NaCl (2), 3-(morpholino) propanesulfonic acid (MOPS sodium salt) (15), $MgSO_4.7H_2O$ (0.2), $FeSO_4.7H_2O$ (0.01), $ZnSO_4.7H_2O$ (0.01), added with 40 micrograms of kanamycin, and incubated in a 300 ml flask at 30° C. and 300 rpm on a rotary shaker for 96–120 hr. The culture is acidified with 250 mg oxalic acid and incubated at 30° C. over night and then extracted with an equal volume of acetonitrile:methanol (1:1) at 30° C. and 300 rpm for 2 hr. The extract is filtered and the filtrate is analyzed by reversed-phase high pressure liquid chromatography (RP-HPLC). RP-HPLC is performed by using a Vydac C18 column (4.6×250 mm; 5 micrometers particle size) at a flow rate of 0.385 ml/min. Mobile phase is 0.2% trifluoroacetic acid (TFA, from Pierce Chemical Co.) in H2O and mobile phase B is 0.078% TFA in acetonitrile (from J: T: Baker Chemical Co.). Elution is performed with a linear gradient from 20 to 60% phase B in phase A in 33 minutes and monitored with a diode array detector set at 488 nm (bandwidth 12 micrometers). ε-rhodomycinone, daunorubicin and doxorubicin (10 micrograms/ml in methanol) are used as external standards to quantitate the amount of these metabolites isolated from the cultures.

EXAMPLES

Example 1

Figure 3:
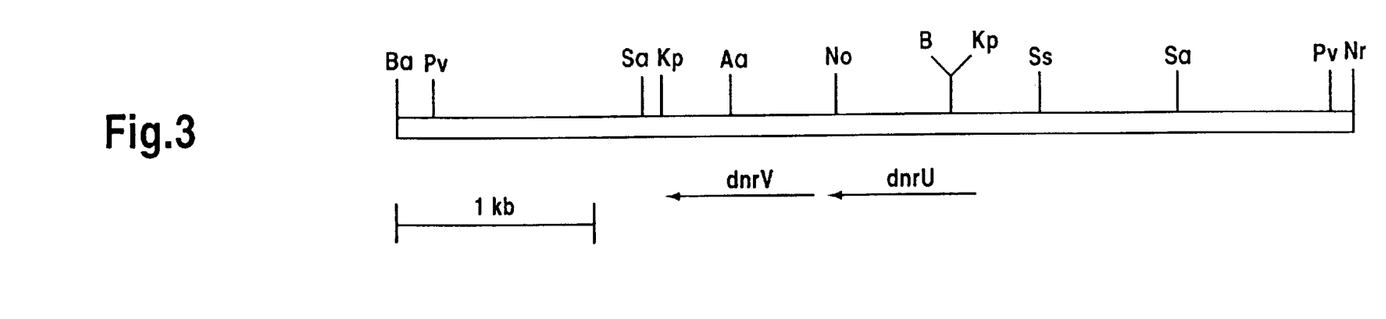
Figure 4:
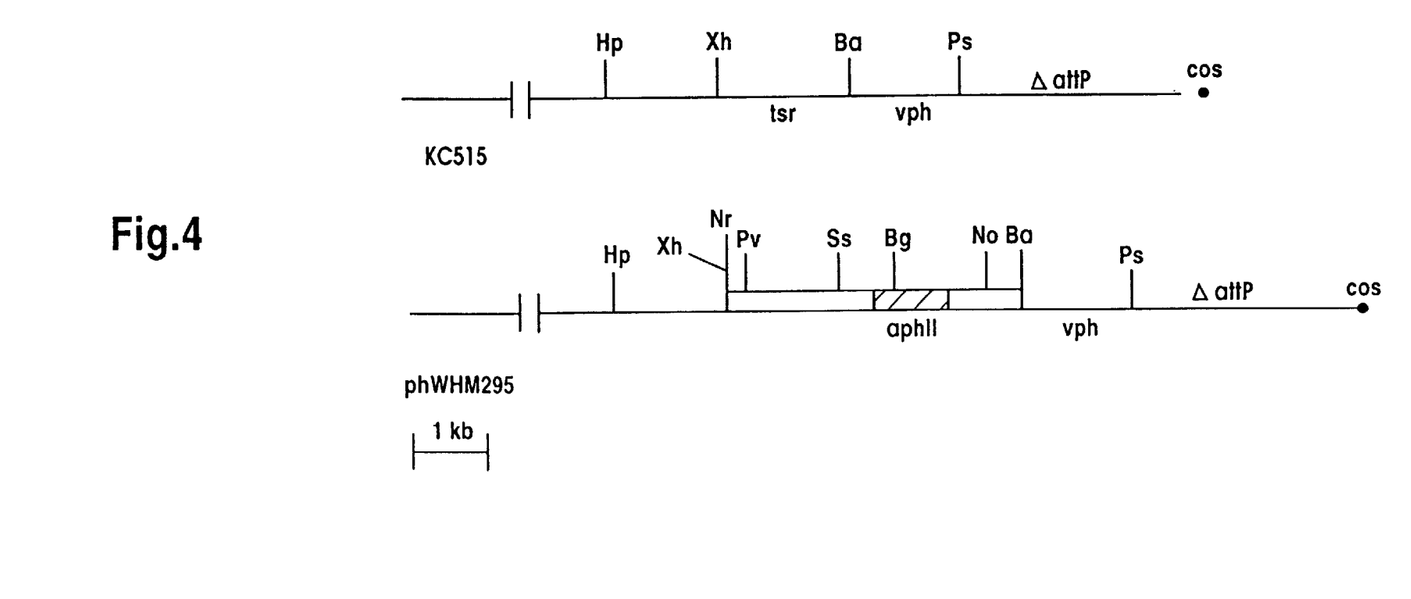

Disruption of dnrU: pWHM555 is constructed by subcloning the 6.0-kb BamHI fragment containing the dnrU and dnrV genes from the pWHM335 cosmid clone described by Stutzman-Engwall and Hutchinson (Proc. Acad. Sci. USA 86: 3135 (1988)) and Otten et al. (J. Bacteriol. 172: 3427 (1990)) in the pUC18 plasmid vector. pWHM289 is constructed by subcloning the 4.8-kb BamHI-NruI fragment containing the dnrU and dnrV genes from pWHM555 in the pSE380 vector, from which a 4.8-kb BamHI-XhoI fragment was cloned into the pSP72 vector to create pWHM290. Then the aphII gene, obtained as a 1.0 kb SalI fragment from pFDNeoS, was inserted into the BalI site located in the beginning of the structural part of dnrU to create pWHM293. A 4.0-kb AatII-XhoI fragment containing the aphII gene was cloned blunt-ended from pWHM293 into the PvuII site of pSP72 to create pWHM294, from which a 4.0-kb BamHI-XhoI fragment containing the disrupted copy of dnrU was cloned into the KC515 phage vector to create phWHM295 (FIG. 3).

Cloning of the dnrU gene: Cloning of S. peucetius 29050 DNA fragments into the phage integrative vector KC515 and screening of the phage carrying a disrupted copy of the dnrU gene are performed as described by Lomovskaya et al. (J. Bacteriol. 178: 3238 (1996) or Microbiology 143: 875 (1997)). The phage plaques obtained after transfection of S. lividans TK24 protoplasts are screened by selection for neomycin resistance with neomycin (10 micrograms/ml) added to R2YE growth medium. The presence or absence of the neomycin (aphII) and viomycin (vph) resistance genes in the phage vector is tested by adding neomycin (10 microgram/ml) and viomycin (200 microgram/ml) to R2YE medium. In this way the phage phWHM295 is characterized as containing aphII and vph resistance genes. The presence of the cloned DNA containing the disrupted dnrU::aphII gene was confirmed by restriction endonuclease digestion analysis.

S. peucetius 29050 is infected with phWHM295 ($5\times10^7$ spores and 1 to $2\times10^8$ phage). After 16 h the plates are overlaid with an aqueous neomycin solution to give a final concentration of 10 microgram/ml, then after further growth for 6 d until sporulation, the plates are replicaplated on minimal medium (Hopwood et al., Genetic Manipulation of Streptomyces. A Laboratory Manual, John Innes Foundation, Norwich, UK, 1985) containing neomycin (10 micrograms/ml). Primary neomycin-resistant clones are isolated and their phenotype is determined after a second round of single colony isolation. Selection for gene replacement is carried out on minimal medium with neomycin (10 micrograms/ml) and viomycin (30 micrograms/ml). In this way, clones are obtained that are resistant to neomycin and sensitive to viomycin. Two colonies with the neomycin-resistance, viomycin-sensitive phenotype are examined by Southern analysis to verify the disruption of the dnrU gene. Chromosomal DNA from the 29050 strain and the WM1658 dnrU mutant strain are digested with BamHI and probed with the 1.1-kb PstI-BamHI fragment of pFDNeoS containing the aphII gene. The probe hybridizes to a 7.0-kb BamHI fragment for the dnrU mutant, which is consistent with the insertion of the aphII gene in the dnrU gene.

Example 2

Enhanced ε-rhodomycinone and doxorubicin production in the fermentation broth of the WHM1658 dnrU::aphII mutant: The dnrU::aphII mutant is grown for 10 days at 30° C. on slants of ISP4 agar medium (Difco) supplemented with 40 micrograms of kanamycin sulfate. The spores of this culture are collected and suspended in 300 ml Erlenmeyer flasks containing 25 ml of R2YE liquid medium containing 40 micrograms of kanamycin sulfate and the flasks are shaken for 2 days at 30° C. on a rotary shaker running at 300 rpm in a 5 cm diameter circle. A 2.5 ml portion of this culture is used to inoculate 25 ml of APM medium containing 40 micrograms of kanamycin sulfate in 300 ml Erlenmeyer flasks. The flasks are incubated at 30° C. for 96 hr under the same conditions described for the seed cultures. The metabolites are extracted from the cultures according to the methods described in the Materials and Methods section. The production values are indicated in Table 1.

TABLE 1

Amount (micrograms/ml) of ε-rhodomycinone, daunorubicin and doxorubicin produced by the S. peucetius ATCC 29050 and WMH1658 dnrU::aphII strains in the APM medium at 96 h.

| Strain | ε-rhodomy-cinone | doxo-rubicin | daunorubicin | doxo/dauno ratio |
|---|---|---|---|---|
| 290950 | 11.6 | 6.6 | 10.1 | 0.65 |
| WMH1658 | 39.4 | 31.7 | 8.9 | 3.56 |

Example 3

Complementation of the dnrU::aphII mutation with the dnrU and dnrU+dnrV genes: To confirm that the high production value of ε-rhodomycinone and doxorubicin in the fermentation broth of the dnrU::aphII mutant is due to dnrU disruption, the WMH1658 dnrU mutant is transformed separately with pWHM299 and pWHM345. These two plasmids are made as follows. A 1.55-kb AatII-SstI fragment from pWHM555 containing the dnrU gene is cloned into pSE380 to create pWHM298. A 1.55-kb EcoRI-HindIII fragment from pWHM298 is cloned into pWHM3 to create pWHM299. A 3.1-kb PvuII-SstI fragment from pWHM555 containing the dnrU and dnrV genes is cloned into pSP72 to create pWHM343. A 3.1-kb EcoRI-XhoI fragment from pWHM343 is cloned into pSE380 to create pWHM344. A 3.1-kb EcoRI-HindIII fragment from pWHM344 is cloned into pWHM3 to create pWHM345. pWHM299 and pWHM345 are introduced separately into the S. peucetius WMH1658 dnrU mutant by the protoplast-mediated transformation method described above, using thiostrepton (20 micrograms/ml) for selection of the transformants. S. peucetius WMH1658 transformants are verified by reisolation of pWHM3, pWHM299 or pWHM345 according to the plasmid isolation protocol described by Hopwood et al. (Genetic Manipulation of Streptomyces. A Laboratory Manual, John Innes Foundation, Norwich, UK, 1985) and analysis of the DNA of these plasmids by restriction endonuclease digestion according to standard protocols (Sambrook et al., Molecular cloning. A Laboratory Manual, 2nd ed. Cold Spring Harbor Press, Cold Spring Harbor, N.Y., 1989). Transformants are grown in the APM medium in the presence of thiostrepton (10 micrograms/ml) and culture extracts are checked for production of ε-rhodomycinone, daunorubicin and doxorubicin production according to the procedure described above. HPLC analysis shows a decrease in the amount of ε-rhodomycinone and doxorubicin produced by the WMH1658(pWHM299) recombinant strain containing the dnrU gene and the WMH1658(pWHM345) recombinant strain containing the dnrU and dnrV genes, compared with the amounts of these metabolites produced by the WMH1658(pWHM3) transformant (typical values are shown in Table 2). As can be seen from Table 2, the complementation experiment with plasmid pWHM345 resulted in a complete restoration of doxorubicin production level. This result is not unexpected since, as already described in Solari et al., *Cloning and Expression of Daunorubicin C-14 Hydroxylase Gene from a Streptomyces peucetius Mutant,* the Sixth Conference on the Genetics and Molecular Biology of Industrial Microorganisms, Oct. 20–24, 1996, Bloomington, Ind., (USA), the presence of the dnrV gene has the effect of increasing the conversion from daunorubicin to doxorubicin in Streptomyces.

TABLE 2

Amounts (micrograms/ml) of ε-rhodomycinone, daunorubicin and doxorubicin produced by the *S. peucetius* WMH1658 *dnrU::aphII* recombinant strain bearing either pWHM3, pWHM299 or pWHM345 in the APM medium at 120 h.

| Strain | ε-rhodomy-cinone | doxo-rubicin | daunorubicin | doxo/dauno ratio |
|---|---|---|---|---|
| WMH1658 (pWHM3) | 75.1 | 70.2 | 30.0 | 2.34 |
| WMH1658 (pWHM299) | 60.3 | 49.4 | 44.1 | 1.12 |
| WMH1658 (pWHM345) | 42.8 | 52.1 | 19.3 | 2.70 |

We claim:

1. An isolated *Streptomyces peucetius* mutant which produces doxorubicin, comprising a daunorubicin metabolism gene dnrU, wherein the function of the dnrU gene has been inactivated.

2. The mutant according to claim 1, wherein said mutant is WMH1658.

3. The mutant according to claim 1, wherein the function of the daunorubicin metabolism gene dnrU is inactivated by insertion of a gene into the dnrU gene.

4. The mutant according to claim 3, wherein the function of the dnrU gene is inactivated by insertion of a neomycin/kanamycin resistance gene aphII.

5. A process for preparing doxorubicin, comprising the steps of:

culturing an isolated *Streptomyces peucetius* mutant comprising a daunorubicin metabolism gene dnrU, wherein the function of the dnrU gene has been inactivated, and isolating doxorubicin from the culture.

6. The process according to claim 5, wherein said *Streptomyces peucetius* is WMH1658.

7. A vector comprising the daunorubicin metabolism gene dnrU, wherein the function of the dnrU gene has been inactivated.

8. The vector according to claim 7, wherein the function of the dnrU gene is inactivated by insertion of an aphII gene.

9. The vector according to claim 7, wherein said vector is a plasmid.

10. A host cell transformed with the vector according to claim 7.

* * * * *